US00PP31920P2

(12) United States Plant Patent
Delabroye

(10) Patent No.: US PP31,920 P2
(45) Date of Patent: Jun. 30, 2020

(54) ***THALICTRUM* PLANT NAMED 'GHENT EBONY'**

(50) Latin Name: *Thalictrum petaloideum*
Varietal Denomination: Ghent Ebony

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 0 days.

(21) Appl. No.: 16/501,240

(22) Filed: Mar. 11, 2019

(30) Foreign Application Priority Data

Jan. 7, 2019 (QZ) ..... PBR 2019/0054

(51) Int. Cl.
*A01H 5/02* (2018.01)
*A01H 6/00* (2018.01)

(52) U.S. Cl.
USPC ..... Plt./263.1
CPC ..... *A01H 6/00* (2018.05)

(58) Field of Classification Search
USPC ..... Plt./263.1
CPC ..... A01H 6/00
See application file for complete search history.

*Primary Examiner* — Anne Marie Grunberg
(74) *Attorney, Agent, or Firm* — Penny J. Aguirre

(57) ABSTRACT

A new cultivar of *Thalictrum* plant named 'Ghent Ebony' that is characterized by its foliage that is dark green-brown in color, its relatively compact plant habit, its flowers that are creamy white in color and its flowering that commences early in the season.

2 Drawing Sheets

Botanical classification: *Thalictrum petaloideum.*
Variety denomination: 'Ghent Ebony'.

BACKGROUND OF THE INVENTION

The present invention relates to a new and distinct cultivar of *Thalictrum petaloideum* of and will be referred to hereafter by its cultivar name 'Ghent Ebony'. *Thalictrum* 'Ghent Ebony' is a deciduous plant grown for use as a landscape plant.

*Thalictrum* 'Ghent Ebony' originated as a seedling that arose from seed planted from open pollination of an unnamed plant of *Thalictrum petaloideum* in March 2011 in Hantay, France. The male parent is therefore unknown. The new *Thalictrum* was selected as a single unique plant in spring of 2012.

Asexual propagation of the new cultivar was first accomplished by tissue culture using meristematic tissue under the direction of the Inventor in May of 2015 in Rijswijk, The Netherlands. Asexual propagation by tissue culture and division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Ghent Ebony' as a unique cultivar of *Thalictrum.*

1. 'Ghent Ebony' exhibits foliage that is dark green-brown in color.
2. 'Ghent Ebony' exhibits a relatively compact plant habit.
3. 'Ghent Ebony' exhibits flowers that are creamy white in color.

4. 'Ghent Ebony' exhibits flowering that commences early in the season.

The female parent of 'Ghent Ebony' differs from 'Ghent Ebony' in having foliage that is green in color. 'Ghent Ebony' can be most closely compared to the *Thalictrum* cultivars 'The Cloud' (not patented) and 'Elin' (not patented). 'The Cloud' is similar to 'Ghent Ebony' in commencing bloom early in the season but differs from 'Ghent Ebony' in having green foliage, a less compact plant habit, and flowers that are pale pink in color. 'Elin' is similar to 'Ghent Ebony' in having similar flowers, but differs from 'Ghent Ebony' in having green foliage, a less compact plant habit, and in commencing bloom later in the season.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1).

BRIEF DESCRIPTION OF THE DRAWINGS

The accompanying colored photographs illustrate the overall appearance and distinct characteristics of the new *Thalictrum*. The photographs were taken of a ten-month-old plant as grown outdoors in a 9-cm container in Boskoop, The Netherlands.

The photograph in FIG. 1 provides a provides a side view of a plant of 'Ghent Ebony' in bloom.

Figure 1:
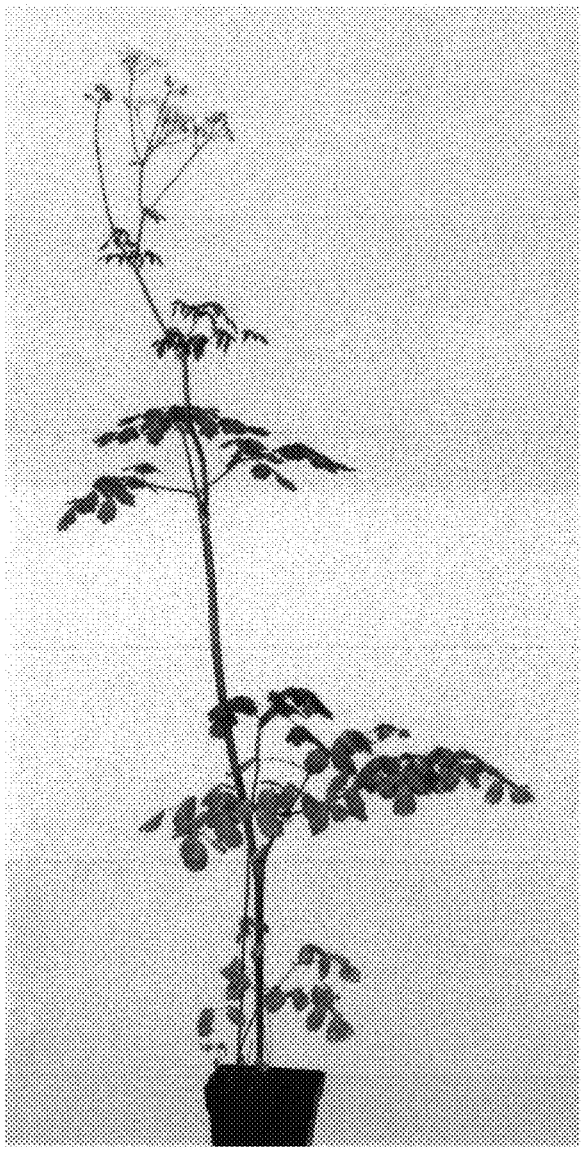
Figure 2:
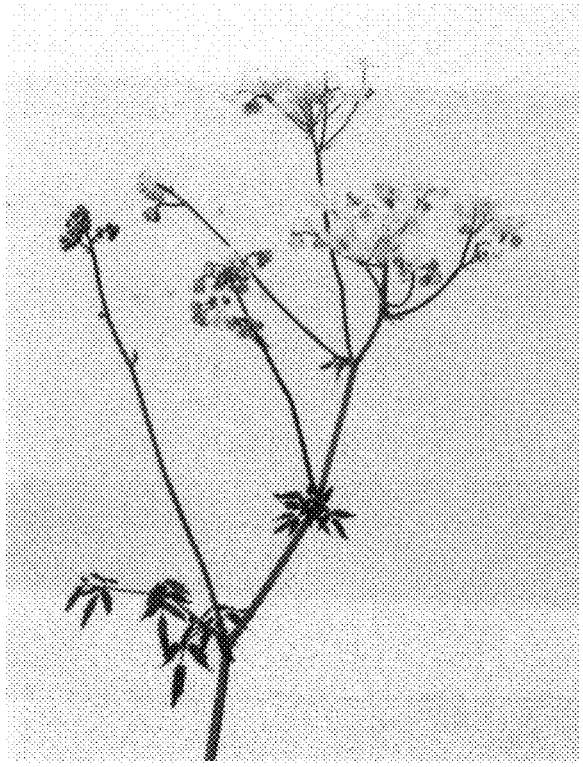

The photograph in FIG. 2 provides a close-up view of the inflorescences of 'Ghent Ebony'. 'Ghent Ebony' in bloom.

Figure 3:
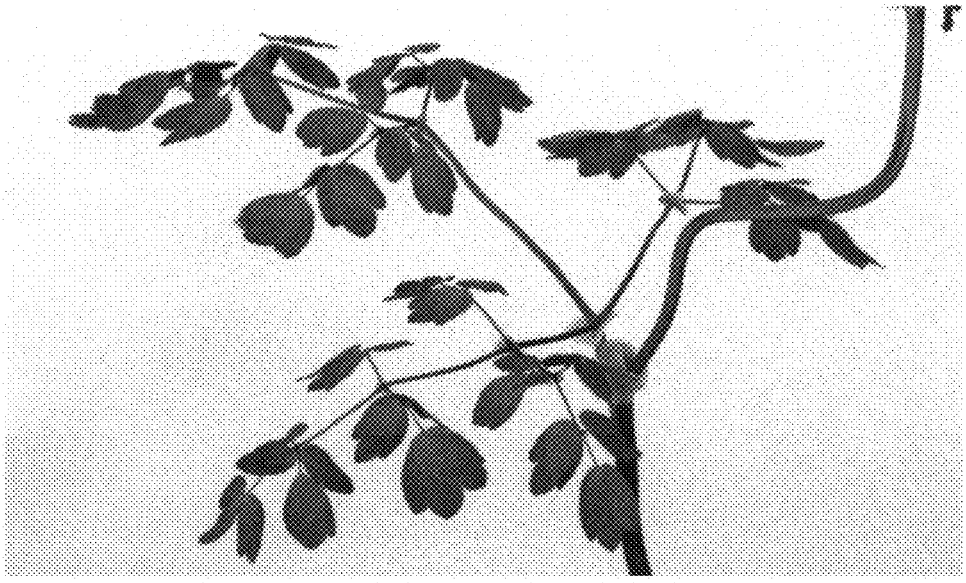

The photograph in FIG. 3 provides a close-up view of the foliage of 'Ghent Ebony'.

The colors of the photographs are as close as possible with the digital photography techniques available, the color values cited in the detailed botanical description accurately describe the colors of the new *Thalictrum*.

DETAILED BOTANICAL DESCRIPTION

The following is a detailed description of ten-month-old plants of 'Ghent Ebony' as outdoors in 9-cm containers in Boskoop, The Netherlands. The phenotype of the new cultivar may vary with variations in environmental, climatic and cultural conditions, as the cultivar has not been tested under all possible environmental conditions. The color determination is in accordance with The 2015 Colour Chart of The Royal Horticultural Society, London, England, except where general color terms of ordinary dictionary significance are used.

General description:

*Blooming period*.—Commences bloom early in season, blooms for 6 weeks from mid May to early July in The Netherlands.

*Plant type*.—Herbaceous perennial.

*Plant habit*.—Upright and relatively compact, flowering stems carry inflorescences above the foliage.

*Height and spread*.—Reaches an average of 1 m in height and 60 cm in width in the landscape.

*Cold hardiness*.—At least in U.S.D.A. Zones 6 to 9.

*Diseases and pests*.—No susceptibility or resistance to diseases or pests has been observed.

*Root description*.—Fibrous, dense, very freely branched, distributed both shallow and deep in soil, smooth and glabrous surface, N199B in color.

*Propagation*.—Tissue culture (preferred) and division.

*Root development*.—An average of 8 weeks to produce a young plant in tissue culture.

*Growth rate*.—Moderate to highly vigorous.

Stem description:

*Shape*.—Slightly oval.

*Stem color*.—Immature; 146B with sunny side tinged 183D, mature; a color between 183A and 187B with shaded side tinged 152C.

*Stem size*.—Average of 56.6 cm in height, an average of 7 mm in width.

*Stem surface*.—Glabrous and slightly ribbed axially.

*Stem number*.—An average of 2 on a plant grown in a 9-cm container.

*Internode length*.—An average of 18.6 cm.

*Stem strength*.—Moderate.

*Branching*.—Emerge from the base.

Foliage description:

*Leaf arrangement*.—Alternate.

*Leaf division*.—Compound; bipinnate to tripinnate.

*Leaf size*.—Up to 30.5 cm in length (excluding petiole) and 31.1 cm in width.

*Leaf attachment*.—Petiolate.

*Leaf shape*.—Broadly ovate.

*Leaflet size*.—An average of 2.9 cm in length and 2.1 cm in width.

*Leaflet shape*.—Obovate.

*Leaflet base*.—Truncate with sheaths; average of 2.6 cm in length and 8 mm in width, 154D in color and tinged towards the petiole 182C.

*Leaflet apex*.—Broad acute.

*Leaflet fragrance*.—None.

*Leaflet venation*.—Pinnate, color on mature leaflets; 200C on upper surface and 148C on lower surface.

*Leaflet margin*.—Tri-lobed, sinuses shallow in depth and divergent in orientation, lobe margins entire.

*Leaflet surface*.—Upper and lower surface smooth, glabrous, matt, non-rugose.

*Leaflet color*.—Young; upper surface 200C to 200D, lower surface a color between 197A and N200B.

*Petioles, petiolules, and rachis*.—Average of 6.3 cm in length, 3 mm in diameter, color between N79C and 187B and strongly tinged with N170C on lower surface, shape round-oval, surface smooth, glabrous, and glossy, petioles; an average of 6.3 cm in length, 3 mm in diameter, petiolules; range from 2 mm to 2.5 cm in length, average of 3 mm in diameter, rachis; an average of 20.5 cm in length, 2 mm in diameter.

*Rachis*.—Average of 20.5 cm in length, 2 mm in diameter, color between N79C and 187B and strongly tinged with N170C on lower surface, shape round-oval, surface smooth, glabrous, and glossy.

*Stipules*.—2 at each rachis node, broadly ovate in shape, connate-perfoliate base, broadly acute apex, an average of 1.4 cm in length and 7 mm in width, smooth and glabrous on both surfaces, margins entire, 154C to 154D in color and slightly to strongly tinged with N77B on both surfaces.

Inflorescence description:

*Inflorescence type*.—Compound corymb.

*Inflorescence arrangement*.—Terminal and axillary nodes.

*Inflorescence size*.—Average of 19 cm in height, 15.4 cm in width.

*Flower buds*.—Broadly ovate in shape, 2 mm in length, 3 mm in diameter, color 147B and axially striped 183A, surface matt, smooth, and glabrous.

*Flower fragrance*.—Moderately faint, somewhat moldy but not unpleasant.

*Lastingness of the flowers*.—An average of 14 days.

*Flower quantity*.—Average of 130 per inflorescence.

*Flower type*.—Comprised of numerous spreading stamens above tepals.

*Flower aspect*.—Upright to outward.

*Flower size*.—1.3 cm in diameter and 1 cm in depth.

*Calyx*.—Cruciform, 2 mm in length and 6 mm in width.

*Tepals*.—4, 4 mm in length, 2 mm in width, elliptic in shape, concave, acute apex, cuneate base, entire margin, color when opening; upper surface N148D and veined with a color close to N77C, lower surface 148C with veins N77C, quickly drop when mature, both surfaces matt, smooth, and glabrous.

*Peduncles*.—Round-oval in shape, average of 14.2 cm in length and 1.75 mm in width, strong, 144B in color with sunny side tinged 200C, held at an average angle of 30° to stem, surface smooth, glossy and glabrous.

*Pedicels*.—Round-oval in shape, average of 1.1 cm in length and 0.5 mm in width, moderate in strength, 146B in color, held at an average angle of 45° to peduncle, surface smooth, glossy and glabrous.

Reproductive organs:

*Gynoecium*.—Average of 8 pistils, average of 0.5 mm in length, stigma; club-shaped, 0.25 mm in length and width, 155A in color, style; 0.25 mm in length, 155A in color, ovary 70C in color.

*Androecium*.—Average of 60 stamens, filaments; average of 6 mm in length, NN155D in color; anthers; oblong in shape, 1 mm in length, 0.5 mm in width, 4C in color, pollen; very low in quantity and 11D in color.

*Seed*.—No seed has been observed to date.

It is claimed:

1. A new and distinct cultivar of *Thalictrum* plant named 'Ghent Ebony' as herein illustrated and described.

* * * * *